United States Patent [19]

Emmer et al.

[11] 4,441,968

[45] Apr. 10, 1984

[54] METHOD OF MANUFACTURE OF AN ELECTRIC HUMIDITY DETECTING SENSING ELEMENT

[75] Inventors: Ivan Emmer; Zdenek Hajek; Petr Repa, all of Prague, Czechoslovakia

[73] Assignee: Matematicko-fyzikalni fakulta University Karlovy v Praze, Prague, Czechoslovakia

[21] Appl. No.: 326,285

[22] Filed: Dec. 1, 1981

Related U.S. Application Data

[63] Continuation-in-part of Ser. No. 158,819, Jun. 12, 1980, abandoned.

[30] Foreign Application Priority Data

Jul. 12, 1979 [CS] Czechoslovakia .............. 4887-79

[51] Int. Cl.$^3$ ............... C25D 11/18; G01N 25/56
[52] U.S. Cl. ............... 204/35 N; 73/335; 204/37 R; 204/38 A; 338/35
[58] Field of Search .............. 204/35 N, 37 R, 38 A; 29/610, 620, 621; 73/335, 336.5; 338/35; 324/61 R

[56] References Cited

U.S. PATENT DOCUMENTS

| | | | |
|---|---|---|---|
| 3,075,385 | 1/1963 | Stover | 73/335 |
| 3,406,106 | 10/1968 | Garwood et al. | 204/37 |
| 3,523,244 | 8/1970 | Goodman et al. | 324/61 |
| 3,861,031 | 1/1975 | Furuichi | 29/610 |
| 3,987,676 | 10/1976 | Bennewitz | 73/336.5 |

Primary Examiner—Winston A. Douglas
Assistant Examiner—William Leader

[57] ABSTRACT

Electric humidity detecting sensing element on the basis of a layer of porous aluminum oxide, treated by sealing in boiling water, passivation and tempering at 70° to 110° C., achieving thereby a substantial reduction of subsequent variations of calibrating curves. The time of tempering may range from 2 to 24 hours. A preferred average time of tempering is 8 hours, with a practical upper limit of 12 hours.

5 Claims, 6 Drawing Figures

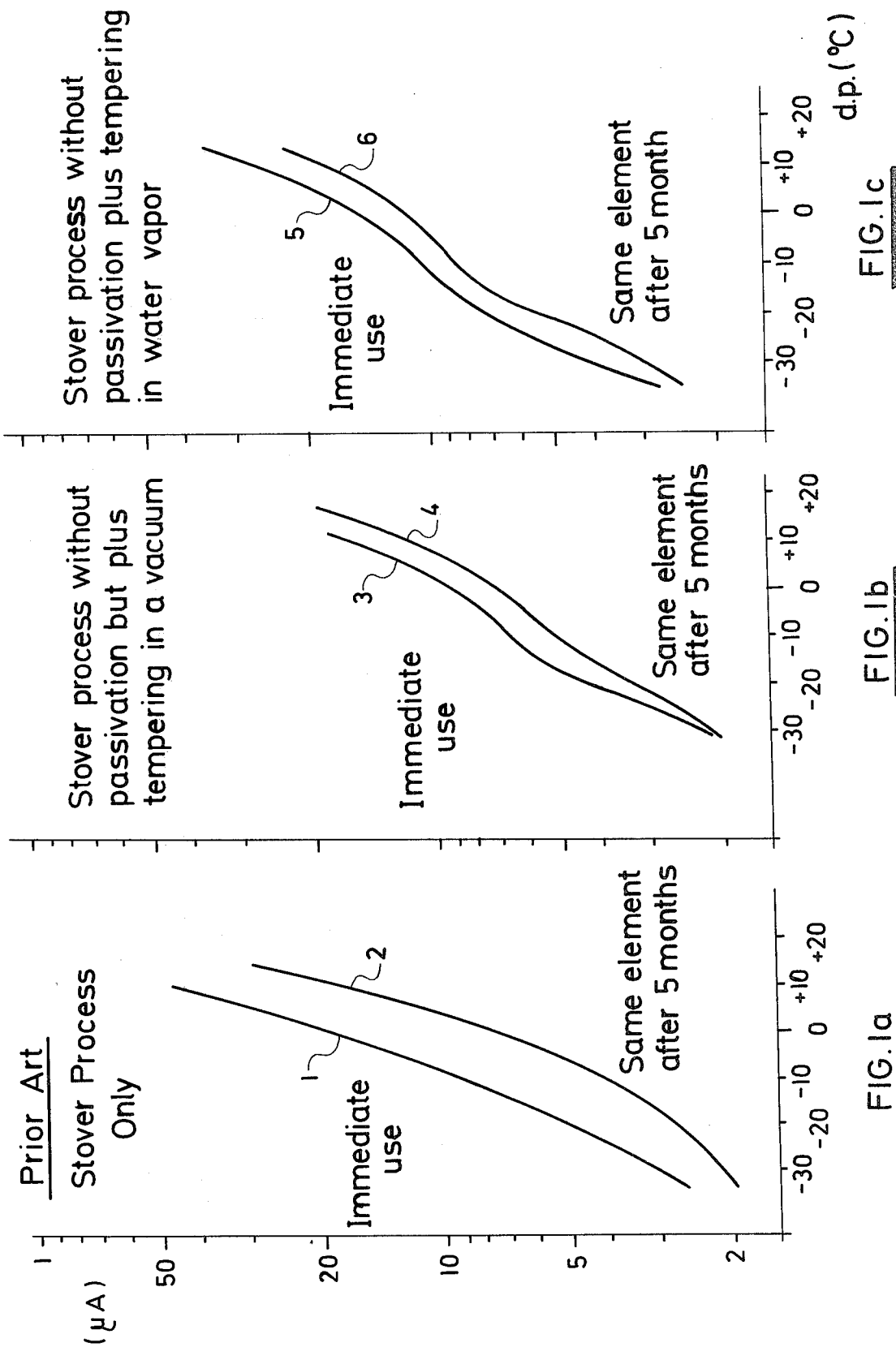

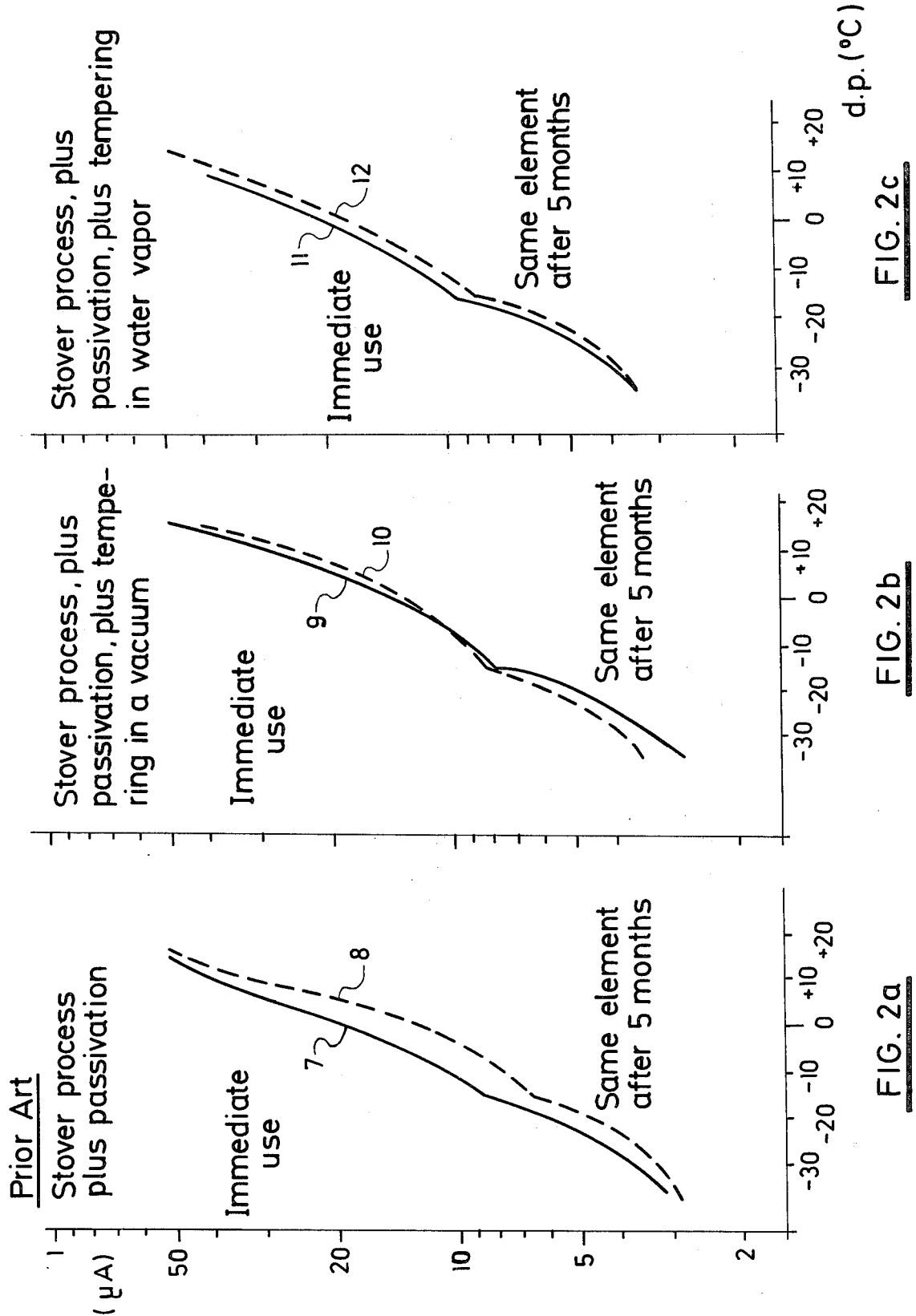

METHOD OF MANUFACTURE OF AN ELECTRIC HUMIDITY DETECTING SENSING ELEMENT

This application is a continuation-in-part of application Ser. No. 158,819, filed June 12, 1980, now abandoned.

BACKGROUND OF THE INVENTION

One of a number of possibilities of measuring the humidity of a medium is the application of sensing elements by means of which the degree of humidity is expressed by an electric signal. Sensing elements with lithium chloride (LiCl), applied with a suitable binding agent on a support, sensing elements with powdered carbon applied with a suitable binding agent on a support, or sensing elements made on the basis of aluminum oxide ($Al_2O_3$) are at present particularly manufactured.

Sensing elements with lithium chloride (LiCl), and those with powdered carbon are sensitive to humidity due to changes of the volume of the layers. Their drawbacks are, however, their slow response to changes of humidity, their unstable calibration curves, and their high dependence on the temperature of the sensing element.

A sensing element on the basis of porous aluminum oxide ($Al_2O_3$) has more favorable properties, as water is absorbed on the surface of pores therein, and thus changes of its electrical properties take place. In this case, we have a surface and not a volume process, and thus the time of response of these sensing elements is therefore shorter. The achievable long-term stability and the resistance of these sensing elements depend on the technology of preparation of the porous layer of aluminum oxide ($Al_2O_3$) and on the subsequent treatment thereof. At present the best results are achieved with sensing elements made according to the Stover process (a process patented by Stover, U.S. Pat. No. 3,075,385, issued Jan. 29, 1963), in which the layer of aluminum oxide ($Al_2O_3$) is obtained by anodic oxidation of a clean polished aluminum surface by alternating current of a density about 12 $mA/cm^3$ using an electrolyte of 50% sulphuric acid ($H_2SO_4$ p.a.) at a temperature of 33° C. for 25 minutes. After rinsing by distilled water, the thus obtained layer is exposed immediately to so-called sealing, which involves immersion in boiling redistilled water for about 30 minutes, after which there is applied on its surface a semi-pervious upper electrode by a suitable method, for instance by vacuum evaporation coating.

A drawback of a thus manufactured sensing element is that in the course of its use the absorbed water acts on the aluminum oxide, causing its gradual hydration, and thus non-reversible changes of the structure of the sensing element and of its properties. These drawbacks can be reduced by passivation of the electric humidity sensing element. The term "passivation" herein used means a specific treatment of the sealed layer of porous aluminum oxide, which treatment prevents its further gradual hydration, without causing any substantial decrease in the porosity of such layer and without destroying its sensitivity to the adsorption of water vapor. The passivation is performed so that the surface of the porous layer of aluminum oxide ($Al_2O_3$) is soaked in an aqueous solution of 0.01 to 2 mol of suitable material, for instance sodium dihydrogen orthophosphate ($NaH_2PO_4.2H_2O$), or silicic acid, at a temperature of 35° to 100° C. for 10 to 60 minutes, in accordance with the Czechoslovakian inventor's certificates Nos. 196,880 and 197,742 to Emmer et al.

SUMMARY OF THE INVENTION

It is an object of this invention to substantially reduce the variations in the calibration curves of electric sensing elements formed on the basis of a porous layer of aluminum oxide. According to this invention, this improvement of the long term stability of calibration curves is obtained as follows: an electric humidity sensing element, provided with a porous layer on the basis of aluminum oxide obtained by oxidation in an electrolyte according to the above-mentioned Stover process is either sealed in boiling water, or sealed and passivated as described, is tempered at a temperature of from 70° to 110° C. for several hours in a suitable atmosphere which is chemically inert to the porous layer of aluminum oxide, before the upper electrode is applied. By the "suitable atmosphere", there is to be understood, for example, a vacuum, or clean air containing water vapor under a lower pressure than that of the water vapor at the temperature of tempering. It is preferred, however, to reduce the amount of water vapor in the tempering atmosphere below the value that corresponds to the dew point of 65° C., as the higher amount of water vapor may cause further uncontrollable sealing of $Al_2O_3$ porous layer, or result in the deterioration of the previous passivation.

An advantage of the method of manufacture of the sensing element according to this invention is that the thus obtained sensing element has a substantially improved long term stability of its calibration curve.

DESCRIPTION OF THE DRAWINGS

The improvements of the calibration stability are illustrated in the attached drawings, in which:

FIGS. 1a, 1b, and 1c are graphs showing the influence of tempering on the calibration stability of a sensing element manufactured according to the Stover process, such process including sealing, and FIGS. 2a, 2b, and 2c are graphs showing the influence of tempering on the stability of a sensing element manufactured according to the Stover process, such process including sealing, which element has been additionally treated by being passivated in a 0.1 mol solution of $NaH_2PO_4.2H_2O$ at a temperature of 90° C. for about 10 minutes.

DESCRIPTION OF PREFERRED METHOD

In all of the graphs of the drawings electric current (vA) is plotted along the ordinate and dew point (d.p.) in degrees C. is plotted along the abscissa. The calibration curve 1 in FIG. 1a shows the course of the magnitude of a signal of a prior art sensing element in dependence on the humidity dew point for a sensing element manufactured according to the Stover process without a subsequent tempering. The calibration curve 2 in FIG. 1a shows the same dependence of the same sensing element measured after five months.

The calibration curves 3 in FIG. 1b and 5 in FIG. 1c, respectively, show the course of the magnitude of the signal of a sensing element in dependence on the dew point, the sensing element having been manufactured according to the Stover process and thereafter, without passivation, being treated by tempering at a temperature of 90° C. in a vacuum (FIG. 1b) and in clean air containing water vapor (FIG. 1c) at a pressure of $2.3.10^4$ p.a. for 8 hours. The calibration curves 4 in FIG. 1b and 6 in FIG. 1c show the same dependence for the respective sensing elements measured after five months.

The calibration curve 7 in FIG. 2a shows the course of the magnitude of the signal of a sensing element in dependence on the humidity dew point for a sensing element manufactured according to the Stover process and passivated in a solution of $NaH_2PO_4.2H_2O$ without subsequent tempering. The calibration curve 8 in FIG. 2a shows the same dependence of the same sensing element measured after five months.

The calibration curves 9 in FIG. 2b and 11 in FIG. 2c show the course of the magnitude of the signal of the sensing element in dependence on the humidity dew point for a sensing element manufactured according to the Stover process, passivated in a $NaH_2PO_4.2H_2O$ solution, and treated according to this invention by tempering it at a temperature of 90° C. in a vacuum (FIG. 2b) and in clean air containing water vapor (FIG. 2c) at a pressure of $2.3.10^4$ p.a. for 8 hours. The calibration curves 10 in FIG. 2b and 12 in FIG. 2c show the same dependence for the sensing elements in FIGS. 2b and 2c, respectively, measured after five months.

The above-mentioned effects and advantages of the object of this invention are due to the fact that by tempering the passivated sensing element the reconstruction of the surface of the active layer of the sensing element is speeded up. Under normal conditions a rather slow adjustment of the layer of aluminum oxide takes place with subsequent long term small changes of sensitivity, the so-called drift of the calibration curve. After application of the process for treatment of the sensing element according to this invention, an active layer with a substantially stable surface is obtained, whereby the drift of the calibration curve is substantially reduced.

Although the invention is illustrated and described with reference to one preferred embodiment thereof, it is to be expressly understood that it is in no way limited to the disclosure of such a preferred embodiment, but is capable of numerous modifications within the scope of the appended claims. Thus the time of tempering may range from 2 to 24 hours. A preferred average time of tempering is 8 hours, with a practical upper limit of 12 hours.

We claim:

1. In a method of manufacturing an electric humidity detecting sensing element by anodically oxidizing a polished aluminum surface by alternating current of a density of about 12 mA/sq.cm using an electrolyte of 50% sulphuric acid at a temperature of 33° C. for 25 minutes to provide a porous layer of aluminum oxide and sealing the porous layer in boiling water, the improvement in combination therewith which comprises prior to preparing an upper electrode, tempering said layer for a time ranging from 2 to 24 hours at a temperature of from 70° to 110° C. in an atmosphere which is chemically inert relative to said aluminum oxide layer, said atmosphere containing water vapor in an amount of from zero to that corresponding to the dew point of 65° C., thereby stabilizing surface properties of said layer with respect to a reversible absorption of water vapor.

2. A method as claimed in claim 1, wherein the said atmosphere is clean air.

3. A method as claimed in claim 1, wherein the tempering takes place in vacuo.

4. A method as claimed in claim 1, wherein the porous aluminum oxide layer, prior to tempering, is passivated by submerging it in an aqueous solution of $NaH_2PO_4.2H_2O$ having a concentration of from 0.01 to 2 mol, for from 10 to 60 minutes at a temperature of from 35° to 100° C.

5. A method as claimed in claim 1, wherein the porous aluminum oxide layer, prior to tempering, is passivated by submerging it in an aqueous solution of pure silicic acid having a concentration of from 0.01 to 2 mol, for from 10 to 60 minutes at a temperature of from 35° to 100° C.

* * * * *